(12) United States Patent
Yamaguchi et al.

(10) Patent No.: US 7,476,261 B2
(45) Date of Patent: Jan. 13, 2009

(54) HAIR DYE COMPOSITION

(75) Inventors: Masakazu Yamaguchi, Sumida-ku (JP);
Dominic Pratt, Darmstadt (DE);
Makiko Aimi, Ashigarakami-gun (JP);
Yasuhiro Ishiwata, Minamiashigara (JP)

(73) Assignees: Kao Corporation, Tokyo (JP);
FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/722,750

(22) PCT Filed: Dec. 20, 2005

(86) PCT No.: PCT/JP2005/023305

§ 371 (c)(1),
(2), (4) Date: Dec. 5, 2007

(87) PCT Pub. No.: WO2006/068104

PCT Pub. Date: Jun. 29, 2006

(65) Prior Publication Data

US 2008/0134448 A1 Jun. 12, 2008

(30) Foreign Application Priority Data

Dec. 24, 2004 (JP) .............................. 2004-374469

(51) Int. Cl.
*A61Q 5/10* (2006.01)
*C07D 285/14* (2006.01)
(52) U.S. Cl. ...................... 8/405; 8/406; 8/426; 8/437; 8/570; 8/571; 8/575; 548/134
(58) Field of Classification Search ...................... 8/405, 8/406, 437, 570, 571, 575; 548/134
See application file for complete search history.

(56) References Cited

FOREIGN PATENT DOCUMENTS

EP     1 550 620    *  8/1979
GB     1 550 620       8/1979

OTHER PUBLICATIONS

STIC Search Report dated Aug. 13, 2008.*
Dal Monte, Dea et al., Dyes from sulfurated benzoheterocyclic compounds: cromium complexes of o, o'-dihydroxy azo compounds. V, Bollerrino Scientifico della Facolta di Chimica idustriale di Bologna, vol. 26, No. 3-4, pp. 215-226, 1968.
U.S. Appl. No. 11/816,422, filed Aug. 16, 2007, Yamaguchi et al.
U.S. Appl. No. 11/722,750, filed Jun. 25, 2007, Yamaguchi et al.
"Benzothiadiazole; Dye; Metallise; Polypropylene; Fibre", IT 778433, WPI Acc No. 1968-35584Q/196800, submitting English Abstract only, 1 page.

* cited by examiner

*Primary Examiner*—Eisa B Elhilo
(74) *Attorney, Agent, or Firm*—Oblon, Spivak, McClelland, Maier & Neustadt, P.C.

(57) ABSTRACT

A hair dye composition containing an azo dye (1) or a salt thereof:

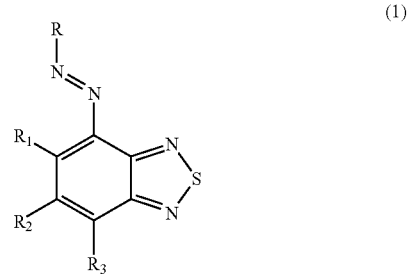

wherein R represents a coupler moiety, $R_1$ and $R_3$ each independently represent $-SO_3M$, $-SO_2NR_4R_5$ or a hydrogen atom, $R_2$, $R_4$ and $R_5$ each independently represent a hydrogen atom or a substituent, and M represents a hydrogen atom, metal atom or ammonium, with a proviso that $R_1$ and $R_3$ are not hydrogen atoms at the same time.

5 Claims, No Drawings

HAIR DYE COMPOSITION

FIELD OF THE INVENTION

This invention relates to a hair dye composition, which contains a direct azo dye including a 2,1,3-benzothiadiazole derivative as an azo moiety can dye hair in a vivid tone, does not fade out, and is stable to alkalizing agents and oxidizing agents

BACKGROUND OF THE INVENTION

Different from permanent hair dye compositions containing oxidative dye intermediates, direct hair dye compositions containing anionic or cationic direct dyes do not require a coupling reaction with an oxidizing agent. They are hence widely applied to hair in the form of so-called color shampoos along with surfactants or in the form of concentrates such as lotions, emulsions or gels. In addition, proposals have also been made on clear hair dyes containing so-called cationic dyes of a construction that a cationic group is contained in a conjugated system.

These direct hair dye compositions are accompanied by a drawback that their colors are vivid shortly after dyeing but substantially fade out with time Moreover, when mixed with an alkaline peroxide commonly employed as an oxidizing agent, these direct dyes are readily decomposed and may not be able to bring about their dyeing effects as expected They, accordingly, involve another drawback that, when employed as hair dyes, such hair dyes are limited to hair dye compositions having no bleaching effects on hair. In addition, they are unstable to alkalizing agents and reducing agents which are essential ingredients for so-called permanent hair dyes containing oxidative dyes, leading to a further drawback that they cannot be used together with such alkalizing agents and reducing agents in permanent hair dyes.

On the other hand, 2,1,3-benzothiadiazole derivatives are compounds known as a kind of azo dyes (see, for example, Patent Document 1, Patent Document 2 and Non-patent Document 1). They are, however all dissatisfactory for use as hair dye compositions from the viewpoints of color hue, fastness and molecular extinction coefficient.

Patent Document 1: GB-A-1550620
Patent Document 2: IT-A-778433
Non-patent Document 1: Bollettino Scientifico della Facolta di Chimica Industriale di Bologna, 26(3-4), 215-216 (1968).

DISCLOSURE OF THE INVENTION

The present invention provides a hair dye composition containing an azo dye or a salt thereof represented by the following formula (1)

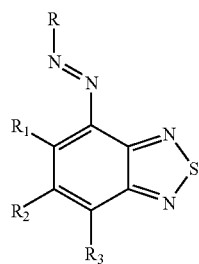

(1)

wherein R represents a coupler moiety, $R_1$ and $R_3$ each independently represent $-SO_3M$, $-SO_2NR_4R_5$ or a hydrogen atom, $R_2$, $R_4$ and $R_5$ each independently represent a hydrogen atom or a substituent, and M represents a hydrogen atom, metal atom or ammonium, with a proviso that $R_1$ and $R_3$ are not hydrogen atoms at the same time.

MODE FOR CARRYING OUT THE INVENTION

This invention relates to a hair dye composition, which can firmly apply a vivid color to hair without causing decomposition of the dye, has excellent resistance to light, wash, perspiration, friction and heat, is stable to alkalizing agents and oxidizing agents, is equipped with high dyeing power, and does not fade out much with time, and also to a hair dying method by making use of the hair dye composition.

The present inventors have found that the hair dye composition containing the azo dye represented by the formula (1) can firmly add a vivid color to hair, which is selected from wide varieties of colors, without causing decomposition of the dye upon dyeing and shows excellent fastness to light, wash, sweat, friction and heat.

The term "substituent" as used herein means a substituent which can substitute for a hydrogen atom. Examples of such substituents include aliphatic hydrocarbon groups (preferably those containing from 1 to 15 carbon atoms, for example, methyl, ethyl, propyl, isopropyl, propargyl, vinyl and the like), aryl groups (preferably those containing from 6 to 16 carbon atoms, for example, phenyl, 4-nitrophenyl, 2,4-dichlorophenyl and the like), heterocyclic groups (preferably those of from 5- to 10-membered rings, for example, 2-tetrahydrofuryl, 2-pyridyl, pyrimidin-2-yl, 1-imidazolyl, 1-pyrazolyl, 2-pyrrolyl, benzothiazol-2-yl, benzimidazol-2-yl and the like), acyl groups (preferably from 1 to 15 carbon atoms, for example, acetyl, 2-methylpropanoyl, pivaloyl, benzoyl and the like), acyloxy groups (preferably those having from 1 to 16 carbon atoms, for example, acetoxy, propanoyloxy, benzolyloxy and the like), acylamino groups (preferably those having from 1 to 8 carbon atoms, for example, acetylamino, propionylamino, 2-methylpropanoylamino, chloroacetylamino, benzamido and the like), aliphatic oxy groups (preferably those having from 1 to 16 carbon atoms, for example, methoxy, ethoxy, butoxy, 2-methoxyethoxy and the like), aryloxy groups (preferably those having from 6 to 17 carbon atoms, for example, phenoxy, 4-nitrophenoxy and the like), heterocycloxy groups (preferably those of from 5- to 10-membered rings, for example, 2-pyridyloxy, 2-furyloxy, 3-pyrazoyloxy and the like), aliphatic oxycarbonyl groups (preferably those having from 1 to 15 carbon atoms, for example, methoxycarbonyl, 2-propyloxycarbonyl, butoxycarbonyl and the like), aryloxycarbonyl groups (preferably those having from 7 to 17 carbon atoms, for example, phenoxycarbonyl, 4-methoxyphenoxycarbonyl and the like), heterocycloxycarbonyl groups (preferably those of from 5- to 10-membered rings, for example, 2-pyridyloxycarbonyl, 2-thienyloxycarbonyl and the like), carbamoyl groups (preferably those having from 1 to 12 carbon atoms, such as carbamoyl, N-ethylcarbamoyl, N,N-dimethylcarbamoyl and the like), aliphatic sulfonyl groups (preferably those having from 1 to 15 carbon atoms, for example, methanesulfonyl, butanesulfonyl, methoxyethanesulfonyl and the like), arylsulfonyl groups (preferably those having from 6 to 16 carbon atoms, for example, phenylsulfonyl, 4-t-butylphenylsulfonyl, p-toluenesulfonyl and the like), heterocyclosulfonyl groups (preferably those of from 5- to 10-membered rings, for example, 2-tetrahydropyranylsulfonyl and the like), aliphatic sulfonyloxy groups (preferably those having from to 15 carbon atoms, for example, methanesulfonyloxy, ethanesulfonyloxy and the like), arylsulfonyloxy groups (preferably those having from 6 to 16 carbon atoms, for example, phenylsulfonyloxy and the like), heterocyclosulfonyloxy groups (preferably those of from 5- to 10-membered rings, for example, 2-pyridylsulfonyloxy and the like), sulfamoyl groups (preferably those having from 0 to 12 carbon atoms, for example, sulfamoyl, N,N-dimethylsulfamoyl and the like), aliphatic sulfonamido groups (preferably those having from 1 to 15 carbon atoms, for example, methanesulfonamido, butanesulfonamido and the like), arylsulfonamido groups (preferably those having from 6 to 16 carbon atoms, for example, benzenesulfonamido, p-toluenesulfonamido and the like), heterocyclosulfonamido groups (those of from 5- to 10-membered rings, for example, 2-pyridylsulfonylamido and the like), amino group, aliphatic amino groups (preferably those containing from 1 to 16 carbon atoms, for example, methylamino, N,N-diethylamino, butylamino and the like), arylamino groups (preferably those having from 6 to 16 carbon atoms, for example, phenylamino and the like), heterocycloamino groups (those of from 5- to 10-membered rings, for example, 2-pyridylamino, pyrazol-4-ylamino, benzimidazol-2-ylamino, benzothiazol-2-ylamino, benzooxazol-2-ylamino, 2-oxazolylamino, 1,2,4-triazol-3-ylamino, 1,2,4-thiadiazol-2-ylamino, 1,3,4-thiadiazol-2-ylamino, 1,2,4-oxadiazol-2-ylamino, 1,3,4-oxadiazol-2-ylamino and the like), aliphatic oxycarbonylamino groups (preferably those having from 2 to 12 carbon atoms, for example, methoxycarbonylamino, ethoxycarbonylamino, t-butoxycarbonylamino and the like), aryloxycarbonylamino groups (preferably those having from 7 to 17 carbon atoms, for example, phenoxycarbonylamino and the like), heterocycloxycarbonylamino groups (those of from 5- to 10-membered rings, for example, 2-pyridyloxycarbonylamino and the like), aliphatic sulfinyl groups (preferably those having from 1 to 12 carbon atoms, for example, methylsulfinyl, butylsulfinyl and the like), arylsulfinyl groups (preferably those having from 6 to 16 carbon atoms, for example, phenylsulfinyl and the like), aliphatic thio groups (preferably those having from 1 to 18 carbon atoms, for example, methylthio, ethylthio, 2-ethoxyethylthio, butylthio and the like), arylthio groups (preferably those having from 6 to 18 carbon atoms, for example, phenylthio and the like), aliphatic oxyamino groups (preferably those having from 1 to 12 carbon atoms, for example, methoxyamino, butoxyamino and the like), aryloxyamino groups (preferably those having from 6 to 16 carbon atoms, for example, phenoxyamino and the like), carbamoylamino groups (preferably those having from 0 to 18 carbon atoms, for example, carbamoylamino and the like), sulfamoylamino groups (preferably those having from 0 to 18 carbon atoms, for example, sulfamoylamino, N,N-dimethylsulfamoylamino and the like) sulfamoylcarbamoyl groups (preferably those having from 1 to 12 carbon atoms, for example, N-(sulfamoyl)carbamoyl, N-(N',N'-dimethylsulfamoyl)carbamoyl and the like), carbamoylsulfamoyl groups (preferably those having from 1 to 12 carbon atoms, for example, N-(carbamoyl)sulfamoyl and the like), dialiphatic oxyphosphinyl groups (preferably those having from 2 to 16 carbon atoms, for example, dimethoxyphosphonyl and the like) diaryloxyphosphinyl groups (preferably those having from 6 to 16 carbon atoms, for example, phenoxyphosphinyl and the like), hydroxy, mercapto, cyano, sulfo, carboxyl, and halogen atoms.

The substituent represented by $R_2$ can be the substituent exemplified above as a substituent in the present invention insofar as it can substitute. $R_2$ may be preferably a hydrogen atom, an aliphatic hydrocarbon group, an aryl group, an acyloxy group, an acylamino group, an aliphatic oxy group, an aliphatic sulfonyloxy group, an arylsulfonyloxy group, an aliphatic sulfonamido group, an arylsulfonamido group an amino group, an aliphatic amino group an arylamino group, an aliphatic oxycarbonylamino group, an aryloxycarbonylamino group, a heterocycloxycarbonylamino group, a hydroxy group, a cyano group a sulfo group, a carbamoylamino group, a sulfamoylamino group or a halogen atom; more preferably a hydrogen atom an aliphatic hydrocarbon group an aryl group, an acyloxy group an aliphatic oxy group, an aliphatic sulfonyloxy group or a halogen atom; more preferably a hydrogen atom.

The substituents represented by $R_4$ and $R_5$ can be the substituents exemplified above as substituents in the present invention insofar as they can substitute. $R_4$ and $R_5$ can each be a hydrogen atom, a linear or branched alkyl group ($C_nH_{2n+1}$) in which n is an integer of from 1 to 6 an alkyl group substituted by one or more hydroxy groups, alkoxy groups having from 1 to 6 carbon atoms, halogen atoms, sulfamoyl groups, sulfonamido groups, carboxy groups, carbamoyl groups, carboxamido groups, alkoxycarbonyl groups or sulfo groups, cycloalkyl groups, a benzyl group, a phenyl group (which may be substituted by one or more hydroxy groups, alkoxy groups having from 1 to 6 carbon atoms, halogen atoms, sulfamoyl groups, sulfonamido groups, carboxy groups, carbamoyl groups, carboxamido groups, alkoxycarbonyl groups or sulfo groups) or a heterocyclic group (which may be substituted by one or more sulfamoyl groups carboxy groups, carbamoyl groups, alkoxycarbonyl groups, sulfo groups or linear or branched alkyl groups ($C_nH_{2n+1}$) in which n is an integer of from 1 to 6); or may form a 5- or 6-membered ring together with the nitrogen atom to which they are bonded. More preferably, $R_4$ and $R_5$ may each be a hydrogen atom or a linear or branched alkyl group ($C_nH_{2n+1}$) in which n is an integer of from 1 to 4. Even more preferably, $R_4$ and $R_5$ may each be a hydrogen atom.

M represents a hydrogen atom, metal atom or ammonium, and as the metal atom, an alkali metal atom or alkaline earth metal atom is preferred. As the alkali metal, lithium, sodium or potassium is preferred, and as the alkaline earth metal, magnesium or calcium is preferred As the ammonium, ammonium, tetramethylammonium, tetraethylammonium, tetrapropylammonium trimethyloctadecylammonium, tetrabutylammonium or benzyltrimethylammonium can be mentioned.

The term "coupler moiety" represented by R means a partial structure derived from a coupler compound which can react with a diazonium salt to obtain an azo dye. This concept is generally used in the field of azo dyes. Preferred as R in the present invention are coupler moieties represented by the below-described formulas (2) to (12), respectively. It is to be noted that they are moieties generally called "phenol couplers", "naphthol couplers", "active methylene couplers", "pyrazolone couplers", "pyrazoloazole couples" and "pyrrolotriazole couplers", respectively. In the formulas (2) to (12), Y indicates a bond coupled with the azo moiety in the formula (1).

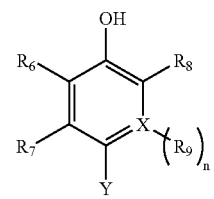

(2)

wherein $R_6$, $R_7$, $R_8$ and $R_9$ each independently represent a hydrogen atom or a substituent or may be fused together to form fused ring(s), X represents a carbon atom or nitrogen atom, and n stands for 1 when X is a carbon atom or n stands for 0 when X is a nitrogen atom.

The substituents represented by $R_6$, $R_7$, $R_8$ and $R_9$ can be the substituents exemplified above as substituents in the present invention insofar as they can substitute. The fused ring(s) can be 5- to 7-membered ring(s) which may be formed through mutual fusion of $R_6$ and $R_7$ and/or $R_8$ and $R_9$ and they may be aromatic ring(s) or non-aromatic ring(s) and may be carbon ring(s) or heterocyclic ring(s) (for example, benzene ring(s) or pyridine ring(s)).

The substituents represented by $R_6$, $R_7$, $R_8$ and $R_9$ can each be a hydrogen atom, aliphatic hydrocarbon group, aryl group, heterocyclic group, acyloxy group, acylamino group, aliphatic oxy group, aryloxy group, heterocycloxy group, aliphatic sulfonamido group, arylsulfonamido group, heterocyclosulfonamido group, amino group, aliphatic amino group, arylamino group, heterocycloamino group, aliphatic oxycarbonylamino group, aryloxycarbonylamino group, heterocycloxycarbonylamino group, aliphatic thio group, arylthio group, hydroxy group, cyano group, sulfo group, carboxyl group, carbamoylamino group, sulfamoylamino group, or halogen atom. More preferably, the substituents represented by $R_6$, $R_7$, $R_8$ and $R_9$ may each be a hydrogen atom, aliphatic hydrocarbon group, heterocyclic group, acylamino group, aliphatic oxy group, aryloxy group, aliphatic sulfonamido group, arylsulfonamido group, aliphatic amino group, arylamino group, heterocycloamino group, aliphatic thio group, arylthio group, or halogen atom.

Among these, the substituents represented by $R_6$ and $R_8$ can each be preferably a substituent selected from a hydrogen atom, a halogen atom, a cyano group, $-CONR_{18}R_{19}$, $-SO_2NR_{18}R_{19}$, $-NHCR_{18}$, $-NHCONR_{18}R_{19}$ or $-NHSO_2NR_{18}R_{19}$. Here, $R_{18}$ and $R_{19}$ each represent a hydrogen atom or a substituent, with a hydrogen atom, an alkyl group having from 1 to 10 carbon atoms, an aryl group having from 6 to 10 carbon atoms or a heterocyclic group having from 1 to 10 carbon atoms being preferred.

On the other hand, the substituents represented by $R_7$ and $R_9$ can each be preferably a hydrogen atom, acylamino group, or halogen atom.

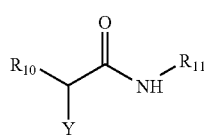

(3)

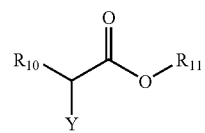

(4)

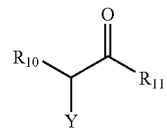

(5)

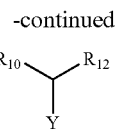

(6)

The formulas (3) to (6) represent couplers called "active methylene couplers" n these formulas, $R_{10}$ represents a substituted or unsubstituted acyl group, cyano group, nitro group, aryl group heterocyclic group, alkoxycarbonyl group, aryloxycarbonyl group carbamoyl group sulfamoyl group, alkylsulfonyl group, or arylsulfonyl group. $R_{11}$ represents a substituted or unsubstituted alkyl group aryl group or heterocyclic group. $R_{12}$ represents a substituted or unsubstituted aryl group or heterocyclic group.

As substituents which $R_{10}$, $R_{11}$ and $R_{12}$ may contain those exemplified above as substituents can be mentioned. In the formulas (3) to (6) $R_{10}$ and $R_{11}$ and $R_{10}$ and $R_{12}$ may be fused together to form rings.

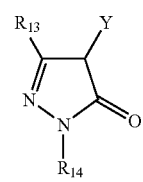

(7)

The formula (7) represents a coupler called a "5-pyrazolone coupler". In this formula, $R_{13}$ represents a cyano group carbamoyl group, alkoxycarbonyl group, acylamino group, arylamino group, alkoxy group, aryloxy group, or alkyl group. $R_{14}$ represents a phenyl group, or a phenyl group substituted by one or more halogen atoms, alkyl groups, cyano groups, alkoxy groups, alkoxycarbonyl groups or acylamino groups

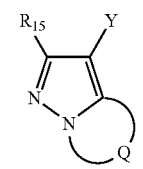

(8)

The formula (8) represents a coupler called a "pyrazoloazole coupler". In this formula, $R_{15}$ represents a hydrogen atom or a substituent. Q represents a non-metal atom group needed to form a 5-membered azole ring which contains from 2 to 4 nitrogen atoms, and such an azole ring may contain one or more substituents (including one or more fused rings).

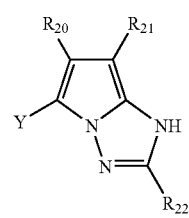

(9)

-continued

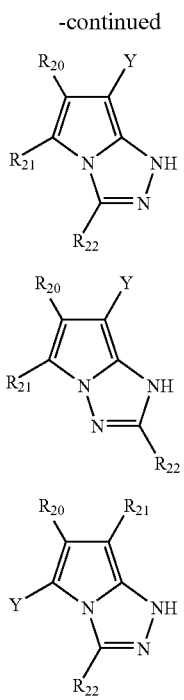

The formulas (9) to (12) represent couplers called "pyrrotriazole couplers". In these formulas, $R_{20}$, $R_{21}$ and $R_{22}$ each represent a hydrogen atom or a substituent. As the substituents represented by $R_{20}$, $R_{21}$ and $R_{22}$, those exemplified above as substituents can be mentioned.

In addition to the formulas (2) to (12), fused-ring phenol couplers, imidazole couplers, pyrrole couplers, 3-hydroxypyridine couplers (the couplers disclosed in JP-A-01-315736, etc.), active methylene couplers other than those represented by the formulas (3) to (6), active methine couplers, 5,5-(fused-ring)heterocyclic couplers 5,6-(fused-ring)heterocyclic couplers and the like are also usable.

As R in the present invention, the coupler moieties represented by the formula (2) are preferred from the standpoint of effects Of these coupler moieties represented by the formula (13) or (14) are more preferred.

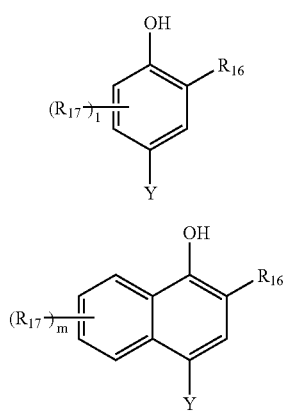

The formula (13) represents couplers called "phenol Couplers", while the formula (14) represents couplers called "naphthol couplers". In these formulas, $R_{16}$ represents a substituent selected from a hydrogen atom, a halogen atom, —$CONR_{18}R_{19}$, —$SO_2NR_{18}R_{19}$, —$NHCOR_{18}$, —$NHCONR_{18}R_{19}$, and —$NHSO_2NR_{18}R_{19}$. Here, $R_{18}$ and $R_{19}$ each represent a hydrogen atom or a substituent, $R_{17}$ represents a substituent, l stands for an integer selected from 0 to 2, and m stands for an integer selected from 0 to 4 When l or m is 2 or greater, the plural $R_{17}$'s may be the same or different.

As the substituents represented by $R_{17}$, $R_{18}$ and $R_{19}$, those exemplified above as substituents can be mentioned. Especially as $R_{18}$ and $R_{19}$, hydrogen atom, alkyl groups having from 1 to 10 carbon atoms, aryl groups having from 6 to 10 carbon atoms, and heterocyclic groups having from 1 to 10 carbon atoms are preferred In the formula (13), $(R_{17})_l$ may preferably be located at the position ortho to the hydroxyl group or para to $R_{16}$ and in the formula (14), $(R_{17})_m$ may preferably be located at the 5-position or 8-position of the naphthol ring.

Specific examples of the azo dye (1) will be shown by the following formulas (D-1) to (D-24).

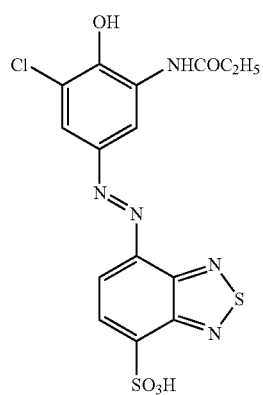

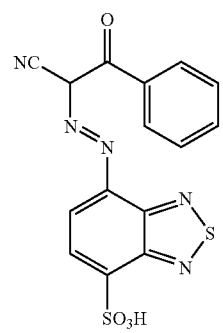

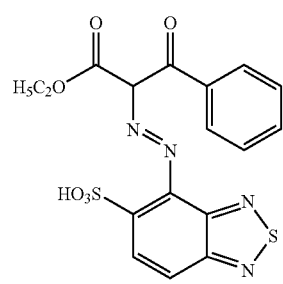

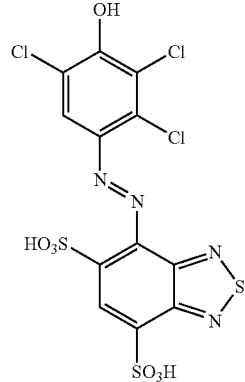
(D-4)
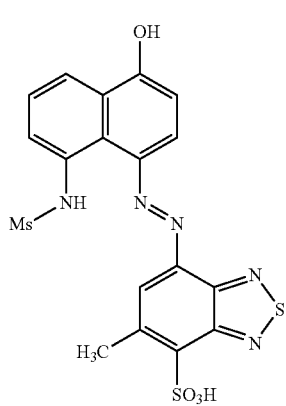
(D-5)
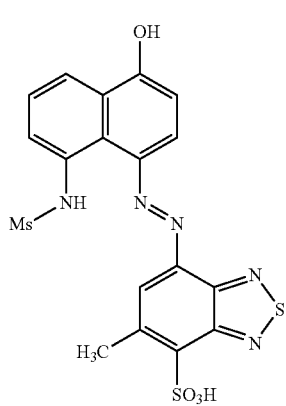
(D-6)
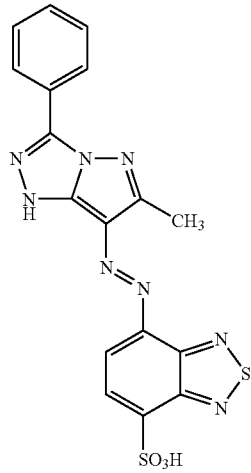
(D-7)
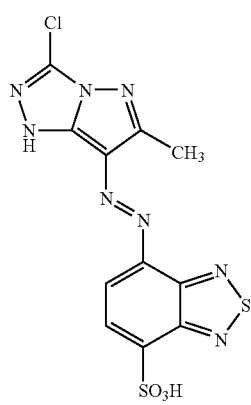
(D-8)
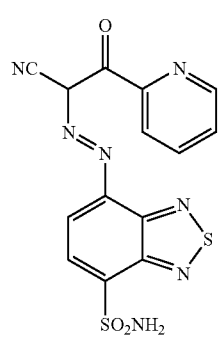
(D-9)
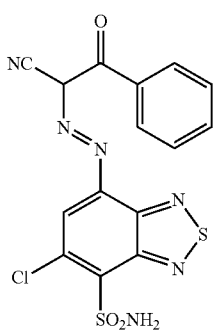
(D-10)

-continued
(D-11)
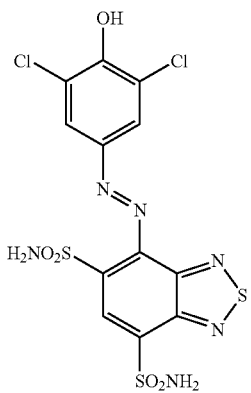
(D-12)
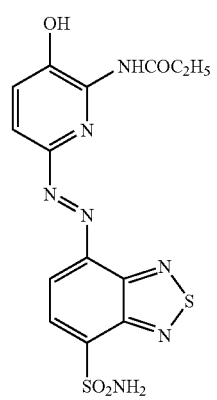
(D-13)
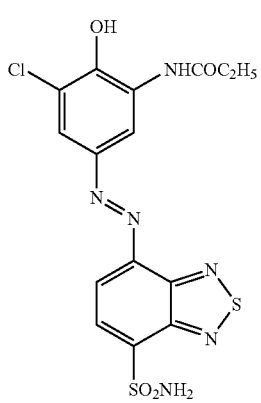
(D-14)
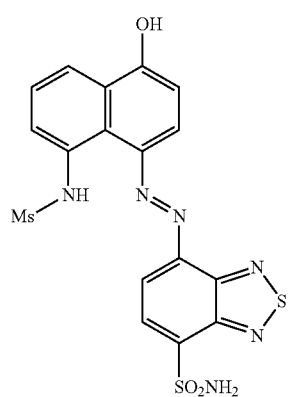
-continued
(D-15)
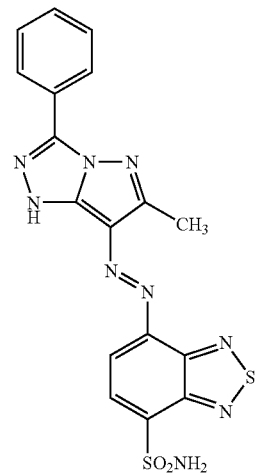
(D-16)
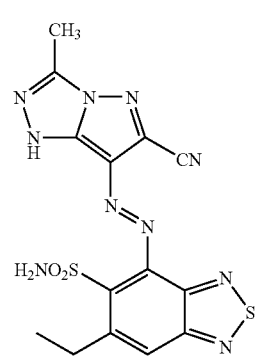
(D-17)
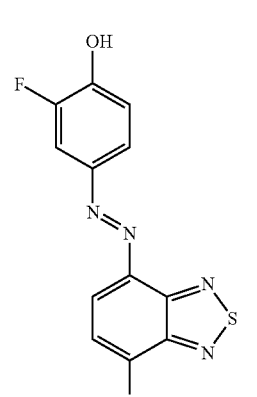
(D-18)
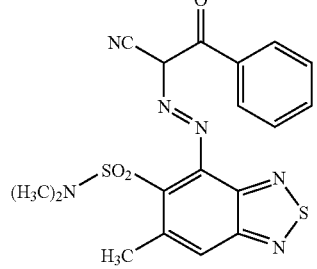

In the formulas (D-6), (D-14), (D-21) and (D-22), Ms represents a methanesulfonyl group The azo dye (1) may be a salt of an inorganic or organic acid or an inorganic or organic alkali. As the inorganic or organic acid hydrochloric acid, sulfuric acid, phosphoric acid, acetic acid, propionic acid, lactic acid or citric acid can be mentioned. As the inorganic or organic alkali, on the other hand ammonium hydroxide, sodium hydroxide, potassium hydroxide, 2-ethanolammonium hydroxide or the like can be mentioned.

The content of the azo dye (1) may be preferably from 0.0001 to 20% by weight, more preferably from 0.001 to 20% by weight, even more preferably from 0.05 to 10% by weight, even more preferably from 0.1 to 5% by weight, all based on the whole composition (in the case of a two-pack or three-pack composition, after the respective packs are combined together. This will equally apply subsequently herein).

As the azo dye (1) is excellent in storage stability over a wide pH range of from 2 to 11 employed in general hair dyes, the hair dye composition according to the present invention can be used at any desired pH within the above range. Nonetheless, it is preferred from the standpoint of dyeing properties to use it within a range of pH 5 and higher. Further, owing to the high stability of the azo dye (1) to alkalizing agents, the hair dye composition according to the present invention can be used at pH8 or higher that provides high dyeing properties, preferably at from pH 8 to pH 11. Even after long-term storage, the direct dye remains free from decomposition so that high dyeing properties can be retained

[Other Dyes]

One or more other direct dyes or oxidative dyes can be added to the hair dye composition according to the present invention to modify the tone.

As other direct dyes, known direct dyes such as basic dyes, cationic dyes, nitro dyes and disperse dyes can be added. More specific examples include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C I. 11055), Basic Red 46 (C.I. 110825), Basic Red 76 (C.I. 12245), Basic Red 118 (C.I. 12251:1), Basic Yellow 28 (C.I. 48054), Basic Yellow 57 (C.I. 12719), the cationic dyes disclosed in JP-A-58-2204, JP-A-09-118832, JP-A-08-501322 and JP-A-0-507545; and cationic methane dyes having the cyanine structure and represented by the following formulas.

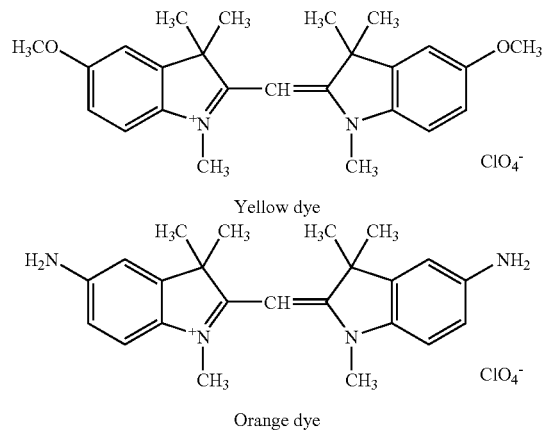

Yellow dye

Orange dye

It is also possible to add, for example, the direct dyes disclosed in JP-A-2002-275040 JP-A-2003-107222, JP-A-2003-107223, JP-A-2003-113055, JP-A-2004-107343, JP-A-2003-342139, and JP-A-2004-155746.

In the hair dye composition according to the present invention, one or more oxidative dyes may also be used in combination with the azo dye (1). Such combined use makes it possible to achieve extremely vivid and intense dyeing which would not be feasible with such oxidative dye or dyes only. As the oxidative dyes known color developers and couplers employed commonly in oxidative hair dyes can be used.

Examples of the color developers include paraphenylenediamine, toluene-2,5-diamine, 2-chloro-paraphenylenediamine N-methoxyethyl-paraphenylenediamine, N,N-bis(2-hydroxyethyl)-paraphenylenediamine, 2-(2-hydroxyethyl)-paraphenylenediamine, 2,6-dimethyl-paraphenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyridine, 2,5,6-triamino-4-hydroxypyrimidine, 4,5-diamino-1-(4'-chlorobenzyl)pyrazole and the like; and salts thereof.

Examples of the couplers include metaphenylenediamine, 2,4-diaminophenoxyethanol, 2-amino-4-(2-hydroxyethylamino)anisole, 2,4-diamino-5-methylphenetol, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaaminophenol, 2-methyl-5-aminophenol, 2-methyl-5-(2-hydroxyethylaminophenol, 2,4-dichloro-3-aminophenol 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcinol, 2-methylresorcinol, 4-chlororesorcinol, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorphorine, 3,4-methylenedioxyphenol, 2-bromo-4,5-methylenedioxyphenol 3,4-methylenedioxyaniline, 1-(2-hydroxyethyl)amino-3,4-methylenedioxybenzene 2,6-dihydroxy-3,4-dimethylpyridine, 2,6-dimethoxy-3,5-diaminopyridine, 2,3-diamino-6-methoxypyridine, 2-methylamino-3-amino-6-methoxypyrine, 2-amino-3-hydroxypyridine, 2,6-diaminopyridine and the like; and salts thereof.

Two or more of these color developers or couplers can be used in combination, and their contents may be preferably from 0.001 to 19% by weight, more preferably from 0.01 to 19% by weight, even more preferably from 0.5 to 10% by weight in total, all based on the whole composition.

To the hair dye composition according to the present invention, one or more autoxidative dyes represented by indoles, indolines or the like can also be added further.

The total content of the azo dye (1) and other dye or dyes in the hair dye composition according to the present invention may be preferably from 0.001 to 20% by weight, more preferably from 0.01 to 20% by weight, even more preferably from 0.5 to 15% by weight, all based on the whole composition.

[Other Ingredients]

Examples of an alkalizing agent for use in the hair dye composition according to the present invention include ammonia; alkanolamines such as monoethanolamine, isopropanolamine and salts thereof; guanidium salts such as guanidine carbonate; hydroxides such as sodium hydroxide; and the like. The content of such an alkalizing agent may be preferably from 0.01 to 20% by weight, more preferably from 0.1 to 10% by weight, even more preferably from 0.5 to 5% by weight, all based on the whole composition.

As the azo dye (1) used in the present invention is extremely stabile to oxidizing agents, it can be applied to hair after it is mixed with an oxidizing agent. In other words, the hair dye composition according to the present invention can be formulated into a two-pack composition consisting of a first pack with the azo dye (1) contained therein (desired one or more of other known direct dye(s) and oxidative dye(s) may also be incorporated) and a second pack with an oxidizing agent contained therein. In this case, dyeing and bleaching are concurrently performed, thereby permitting more vivid dyeing Examples of such oxidizing agents include hydrogen peroxide; persulfates such as ammonium persulfate, potassium persulfate and sodium persulfate; perborates such as sodium perborate; percarbonates such as sodium percarbonate; bromates such as sodium bromate and potassium bromate; and the like. Among these, hydrogen peroxide is preferred from the standpoints of bleaching properties to hair and the stability and effectiveness of the azo dye (1). Along with hydrogen peroxide, another oxidizing agent can be used as an oxidation aid in combination Combined use of hydrogen peroxide and a persulfate is preferred.

The content of an oxidizing agent may be preferably from 0.5 to 30% by weight, more preferably from 1 to 20% by weight, both based on the whole composition. When hydrogen peroxide and a persulfate are used in combination, the content of hydrogen peroxide may preferably be from 0.5 to 10% by weight based on the whole composition, the content of the persulfate may preferably be from 0.5 to 25% by weight based on the whole composition; and the total content of both of them may preferably be from 1 to 30% by weight.

The mixing ratio of the first pack, which contains the azo dye (1), to the second pack, which contains the oxidizing agent, my preferably be in a range of from 2:1 to 1:3 by volume.

In combination with a known two-pack oxidative hair dye or bleach composed of a first pack containing an alkalizing agent (which may also contain optionally one or more of other known direct dyes) and a second pack containing an oxidizing agent, or a known three-pack oxidative hair dye or bleach composed of a first pack containing an alkalizing agent (which may also contain optionally one or more of other known direct dyes), a second pack containing an oxidizing agent and a third pack containing an oxidation additive, a single-pack hair dye composition containing the azo dye (1) can additionally be used either before use or during use to modify the tone of the oxidative hair dye.

The dyeing properties and shampoo fastness of the azo dye (1) can be further improved by adding, to the hair dye composition an organic solvent having hair penetration ability which is selected from an aromatic alcohol, lower alkylene carbonate, N-alkylpyrrolidone or formamide. Examples of the aromatic alcohol include benzyl alcohol, phenethyl alcohol, γ-phenylpropyl alcohol, cinnamic alcohol anise alcohol, p-methylbenzyl alcohol, α,α-dimethylphenethyl alcohol, α-phenyletharol, phenoxyethanol, and the like. Examples of the lower alkylene carbonate include carbonates having alkylene groups of from 2 to 6 carbon atoms such as ethylene carbonate, propylene carbonate and butylene carbonate, examples of the N-alkylpyrrolidone include N-methylpyrrolidone, N-ethylpyrrolidone and the like, and examples of the formamide include N-cyclohexylformamide, N,N-dimethylformamide, N-methylformamide and the like. From the standpoints of dyeing properties and shampoo fastness benzyl alcohol, benzyloxyethanol, propylene carbonate and the like are preferred Two or more of such organic solvents may be used in combination, and from the standpoints of dyeing properties and shampoo fastness, its content may be preferably from 1 to 50% by weight, more preferably from 5 to 45% by weight.

Addition of polyols, polyolalkyl ethers, cationic or amphoteric polymers or silicones to the hair dye composition according to the present invention is preferred, because uniform dyeing properties can be obtained and hair cosmetic effects can be improved.

In addition to the above-described ingredients other ingredients commonly employed as cosmetic ingredients can also be added to the hair dye composition according to the present invention As such optional ingredients, hydrocarbons, animal or botanical oils and fats, higher fatty acids, penetration promoters, cationic surfactants, natural or synthetic polymers, higher alcohols, ethers, amphoteric surfactants, nonionic surfactants, anionic surfactants, protein derivatives amino acids, preservatives, cheating agents, stabilizers, antioxidants, botanical extracts, crude dug extracts, vitamins, colorants, fragrances, ultraviolet absorbers and the like can be mentioned The hair dye composition according to the present invention can be formulated by a method known per se in the art into a single-pack composition, a two-pack composition consisting of a first pack containing an alkalizing agent and a second pack containing an oxidizing agent, or a three-pack composition including a powdery oxidizing agent such as a persulfate in addition to these two packs. The azo dye (1) can be incorporated in either one or both of the packs in the two-pack or three-pack composition. When the hair dye composition is a single-pack form, the hair dye composition is applied directly to hair. In the case of the hair dye composition in a two-pack or three-pack form, on the other hand, the hair dye composition is applied to hair after mixing its ingredients upon dyeing. As an alternative upon mixing the two-pack or three-pack composition, the single-pack composition containing the direct dye (1) may be also mixed and may then be applied to the hair.

Its form can be a powder, clear liquid, emulsion, cream, gel, paste, aerosol, aerosol foam or the like. Its viscosity at the stage of its application to the hair may be preferably from 1,000 to 100,000 mPa·s, more preferably from 5,000 to 50,000 mPa·s, even more preferably from 10,000 to 40,000 mPa·s. It is to be noted that the viscosity is a value measured at 20° C. by using a Brookfield rotational viscometer (No. 5 spindle, 5 rpm)

The hair dye composition according to the present invention can be used to dye human or animal hair. Such a dyeing method comprises applying the hair dye composition to hair, shampooing the hair subsequent to the completion of the dyeing, and drying the hair after the shampooing.

EXAMPLES 1-5

Following a common procedure, the single-pack hair dyes shown in Table 1 were formulated.

TABLE 1

| (% by weight) | Examples | | | | |
| --- | --- | --- | --- | --- | --- |
| | 1 | 2 | 3 | 4 | 5 |
| Dissociative direct dye (D-1) | 0.3 | — | 0.1 | 0.1 | 0.1 |
| Dissociative direct dye (D-13) | — | 0.2 | — | 0.2 | — |
| Dissociative direct dye (D-14) | — | 0.2 | — | 0.2 | — |
| HC Red 3 | — | — | 0.2 | 0.2 | 0.2 |
| Basic Blue 99 | — | — | — | — | 0.1 |
| Ammonia (28% by weight) | 8.0 | 8.0 | 8.0 | 8.0 | 8.0 |
| Isopropyl alcohol | 1.5 | 1.5 | 1.5 | 1.5 | 1.5 |
| Ethanol | 6.0 | 6.0 | 6.0 | 6.0 | 6.0 |
| Benzyl alcohol | 8.0 | 8.0 | 8.0 | 8.0 | 8.0 |
| PEG-12 | — | — | — | — | — |
| Ammonium chloride*[1] | q.s. | q.s. | q.s. | q.s. | q.s. |

TABLE 1-continued

|  | Examples | | | | |
|---|---|---|---|---|---|
| (% by weight) | 1 | 2 | 3 | 4 | 5 |
| Hydroxypropyl xanthan gum | 2.0 | 2.0 | 2.0 | 2.0 | 2.0 |
| Polyether-modified silicone*2 | — | 1.5 | 1.5 | — | 1.5 |
| Purified water | Balance | Balance | Balance | Balance | Balance |
| Total | 100.0 | 100.0 | 100.0 | 100.0 | 100.0 |

*1 Amount sufficient to adjust pH to 10
*2 "KF-6005", Shin-Etsu Chemical Co., Ltd.

The above-described single-pack hair dyes were applied at 30° C. to swatches of goat hair, respectively, and after an elapse of a 20-minute acting time, the swatches of goat hair were washed with an ordinary shampoo and then dried. The resultant swatches of goat hair were observed for tone. As a result, they were all good in dyeing properties and shampoo fastness.

EXAMPLES 6-10

Following common procedures, the first packs of the creamy two-pack hair dyes shown in Table 2 and their common second pack presented in Table 3 were formulated.

TABLE 2

|  | Examples | | | | |
|---|---|---|---|---|---|
| (% by weight) | 6 | 7 | 8 | 9 | 10 |
| Dissociative direct dye (D-1) | 0.3 | 0.3 | 0.1 | 0.1 | 0.1 |
| Dissociative direct dye (D-13) | — | — | — | 0.1 | — |
| Dissociative direct dye (D-14) | — | 0.2 | — | 0.2 | 0.2 |
| Paraaminophenol | 0.3 | 0.1 | — | 0.1 | — |
| Toluene-2,5-diamine sulfate | 0.2 | — | 0.2 | — | 0.3 |
| 5-Aminoorthocreasol | 0.1 | — | 0.2 | 0.1 | — |
| Metaaminophenol | 0.2 | 0.1 | — | — | 0.3 |
| Ammonia (28% by weight) | 8.0 | 8.0 | 8.0 | 8.0 | 8.0 |
| Stearyl alchol | 8.0 | 8.0 | 8.0 | 8.0 | 8.0 |
| Coconut fatty acid monoethanolamide | 4.5 | 4.5 | 4.5 | 4.5 | 4.5 |
| Glyceryl stearate (SE) | 1.3 | 1.3 | 1.3 | 1.3 | 1.3 |
| Coconut fatty alcohol polyglycol ether*3 | 4.0 | 4.0 | 4.0 | 4.0 | 4.0 |
| Sodium laurylacetate | 1.0 | 1.0 | 1.0 | 1.0 | 1.0 |
| Oleic acid | 2.0 | 2.0 | 2.0 | 2.0 | 2.0 |
| 1,2-Propanediol | 1.5 | 1.5 | 1.5 | 1.5 | 1.5 |
| Polyether-modified silicone*4 | 1.5 | — | — | 1.5 | 1.5 |
| Protein hydrolyzate | 0.5 | 0.5 | 0.5 | 0.5 | 0.5 |
| Panthenol | 0.8 | 0.8 | 0.8 | 0.8 | 0.8 |
| Tetrasodium edetate | 0.5 | 0.5 | 0.5 | 0.5 | 0.5 |
| Ammonium chloride*5 | q.s. | q.s. | q.s. | q.s. | q.s. |
| Purified water | Balance | Balance | Balance | Balance | Balance |
| Total | 100.0 | 100.0 | 100.0 | 100.0 | 100.0 |

*3 "SETEARETH-30"
*4 "KF-6005", Shin-Etsu Chemical Co., Ltd.
*5 Amount sufficient to adjust pH to 10

TABLE 3

| (% by weight) | Common second pack |
|---|---|
| Cetanol | 2.0 |
| Sodium laurylsulfate | 1.0 |
| Hydrogen peroxide (50% by weight) | 12.0 |
| Methylparabene | 0.1 |
| Phosphoric acid | Amount sufficient to adjust pH to 3.5 |
| Purified water | Balance |
| Total | 100 |

After the common second pack (1 parts by weight) was mixed with the respective first packs (1 parts by weight, the resultant creamy two-pack hair dyes were applied at 30° C. to swatches of goat hair, and after an elapse of a 30-minute acting time, the swatches of goat hair were washed with an ordinary shampoo and then dried. The resultant swatches of goat hair were observed for tone. As a result, they were all good in dyeing properties and shampoo fastness.

The invention claimed is:

1. A hair dye composition comprising an azo dye or a salt thereof represented by the following formula (1):

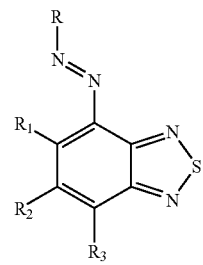

(1)

wherein R represents a coupler moiety, $R_1$ and $R_3$ each independently represent —$SO_3M$, —$SO_2NR_4R_5$ or a hydrogen atom, $R_2$, $R_4$ and $R_5$ each independently represent a hydrogen atom or a substituent, and M represents a hydrogen atom metal atom or ammonium, with a proviso that $R_1$ and $R_3$ are not hydrogen atoms at the same time.

2. The hair dye composition according to claim 1, wherein R is a group represented by the following formula (2):

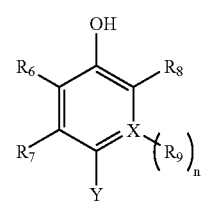

(2)

wherein Y represents a bond coupled with an azo moiety in the formula (1), $R_6$, $R_7$, $R_8$ and $R_9$ each independently represent a hydrogen atom or a substituent or may be fused together to form a fused ring, X represents a carbon atom or nitrogen atom, and n stands for 1 when X is a carbon atom or n stands for 0 when X is a nitrogen atom.

3. The hair dye composition according to claim 1 or 2, further comprising an oxidizing agent.

4. The hair dye composition according to any one of claims 1-3, further comprising an oxidative dye.

5. The method for dyeing hair, which comprises applying the hair dye composition according to any one of claims 1-4 to the hair.

* * * * *